United States Patent [19] [11] 4,020,075
Alaimo et al. [45] Apr. 26, 1977

[54] 2-BROMO-1-HYDROXYQUINOLIZINIUM BROMIDE SUBSTITUTED ANILINIUM SALTS

[75] Inventors: Robert J. Alaimo; Marvin M. Goldenberg, both of Norwich, N.Y.

[73] Assignee: Morton-Norwich Products, Inc., Norwich, N.Y.

[22] Filed: May 13, 1974

[21] Appl. No.: 469,472

[52] U.S. Cl. .................. 260/296 B; 260/295 F; 424/263

[51] Int. Cl.² ........................ C07D 471/00

[58] Field of Search ............... 260/296 B, 295 F

[56] References Cited

UNITED STATES PATENTS 3,780,048  12/1973  Alaimo et al. ............... 260/296 B Primary Examiner—Alan L. Rotman
Attorney, Agent, or Firm—Anthony J. Franze

[57] ABSTRACT

2-Bromo-1-hydroxyquinolizinium bromide substituted anilinium salts are useful as antiinflammatory agents.

7 Claims, No Drawings

2-BROMO-1-HYDROXYQUINOLIZINIUM BROMIDE SUBSTITUTED ANILINIUM SALTS

This invention relates to 2-bromo-1-hydroxyquinolizinium bromide substituted anilinium salts, particularly those of the formula:

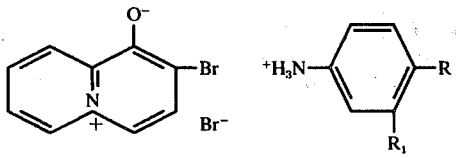

wherein R is methoxy, ethoxy, phenoxy or allyloxy and $R_1$ is hydrogen or methoxy.

These compounds are antiinflammatory agents. When administered perorally to rats in an aqueous suspension followed by the subplantar injection of 0.05 ml. of a 1% solution of carrageen (Viscarin) into the hindfoot of said rats, they cause a marked reduction in edema. This useful antiinflammatory effect in a standardized test for detecting such property makes them desirable agents in counteracting inflammation.

The method for preparing the compounds of this invention which is presently preferred consists in reacting 1-acetoxy-2-bromoquinolizinium bromide with the appropriate aniline in a suitable solvent such as isopropanol and advantageously under the influence of heat.

In order that this invention may be readily understood by and available to those skilled in the art, the following examples are set forth.

EXAMPLE I

2-Bromo-1-hydroxyquinolizinium bromide p-phenetidinium salt

To a solution of 1-acetoxy-2-bromoquinolizinium bromide (30.0 g., 0.09 mole) in isopropanol (600 ml.) was added p-phenetidin (24.0 g., 0.18 mole). The stirred mixture was boiled under reflux for 4 hours, during which time solid had precipitated from solution. The cooled mixture was filtered and washed with ether. The product as yellow needles weighed 37.0 g. (97%). Recrystallization from alcohol-ether provided yellow needles which melted at 161°–162°.

Anal. Calcd. for $C_{17}H_{18}Br_2N_2O_2$: C, 46.18; H, 4.10; N, 6.34; Br, 36.15;

Found: C, 46.20 H, 4.30; N, 6.42; Br, 35.92, 35.85.

EXAMPLE II

2-Bromo-1-hydroxyquinolizinium bromide p-anisidinium salt

Into a 500 ml., 3-neck flask was placed a mixture of 1-acetoxy-2-bromoquinolizinium bromide (12.0 g., 0.035 mole), p-anisidine (9.6 g., 0.078 mole) and isopropanol (240 ml.). The stirred solution was boiled under reflux for 4.5 hours. After cooling in an ice bath the reaction mixture was treated with ethyl acetate to induce crystallization. The yellow solid (11.0 g., 74%) was removed by filtration, washed with ether and ethyl acetate and dried at 63°. Recrystallization from isopropanol/ethyl actate provided a pale yellow powder which melted at 129°–133°.

Anal. Calcd. for $C_{16}H_{16}Br_2N_2O_2$: C, 44.88; H, 3.77; N, 6.54; Br, 37.33;

Found: C, 44.70, 44.74; H, 3.70, 3.83; N, 6.57, 6.63; Br, 37.16, 37.07.

EXAMPLE III

2-Bromo-1-hydroxyquinolizinium bromide p-phenoxyanilinium salt

To a solution of 1-acetoxy-2-bromoquinolizinium bromide (12.0 g., 0.035 mole) in isopropanol (250 ml.) was added p-phenoxyaniline (15.0 g., 0.08 mole). The stirred mixture was boiled under reflux for 3.5 hours. The reaction mixture was treated with ether and scratched, and the precipitate was removed by filtration and dried at 63°. The mustard-yellow product weighed 11.0 g. (65%). Recrystallization from isopropanol/ether provided gold crystals melting at 123°–125°.

Anal. Calcd. for $C_{21}H_{18}Br_2N_2O_2$: C, 51.45; H, 3.70; N, 5.72; Br, 32.61;

Found: C, 51.52, 51.42; H, 3.69, 3.74; N, 5.65, 5.72; Br, 32.70, 32.77.

EXAMPLE IV

2-Bromo-1-hydroxyquinolizinium bromide p-allyloxyanilinium salt

To a solution of 1-acetoxy-2-bromoquinolizinium bromide (10.0 g., 0.029 mole) in isopropanol (200 ml.) was added p-allyloxyaniline (11.0 g., 0.068 mole). The stirred mixture was boiled under reflux for 4.5 hours. The reaction mixture was cooled at room temperature overnight, and the solid was removed by filtration and washed with ether, providing 5.0 g. of product. The supernatant solution was treated with ether and refrigerated, providing another 5.0 g. of product, making the total yield 10.0 g. (77%). Recrystallization from isopropanol produced a light yellow powder melting at 125°–127°.

Anal. Calcd. for $C_{18}H_{18}Br_2N_2O_2$: C, 47.60; H, 3.99; N, 6.17; Br, 35.19;

Found: C, 47.69; 47.70; H, 4.09, 4.17; N, 6.12, 6.15; Br, 34.41, 34.26.

EXAMPLE V

2-Bromo-1-hydroxyquinolizinium bromide 3,4-dimethoxyanilinium salt

To a solution of 1-acetoxy-2-bromoquinolizinium bromide (10.0 g., 0.029 mole) in isopropanol (200 ml.) was added 4-aminoveratrole (10.0 g., 0.65 mole). The stirred mixture was boiled under reflux for 4.5 hours. The reaction mixture was cooled overnight at room temperature, and the solid was then removed by filtration. The green product was suspended in ether and filtered again. It weighed 10.0 g. after having dried at 63°. Recrystallization from alcohol provided a light green analytical sample melting at 160°–162°.

Anal. Calcd. for $C_{17}H_{18}Br_2N_2O_3$: C, 44.56; H, 3.96; N, 6.12; Br, 34.89;

Found: C, 44.80; 44.56; H, 4.01, 4.05; N, 5.96, 5.96; Br, 34.88, 34.73.

What is claimed is:

1. A compound of the formula:

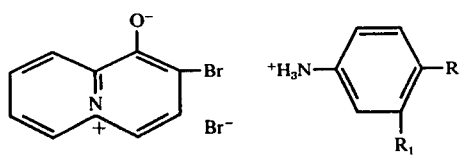

wherein R is methoxy, ethoxy, phenoxy or allyloxy and $R_1$ is hydrogen or methoxy.

2. The compound of claim 1 wherein R is methoxy and $R_1$ is hydrogen.
3. The compound of claim 1 wherein R is ethoxy and $R_1$ is hydrogen.
4. The compound of claim 1 wherein R is phenoxy and $R_1$ is hydrogen.
5. The compound of claim 1 wherein R is allyloxy and $R_1$ is hydrogen.
6. The compound of claim 1 wherein R is methoxy and $R_1$ is methoxy.
7. The method of preparing a compound of the formula:

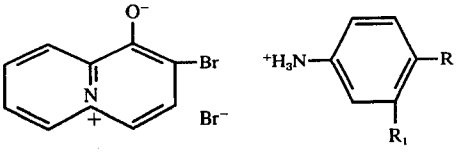

wherein R is methoxy, ethoxy, phenoxy or allyloxy and $R_1$ is hydrogen or methoxy with comprises reacting 1-acetoxy-2-bromoquinolizinium bromide with an aniline of the formula:

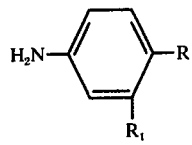

wherein R and $R_1$ have the aforeassigned significance.

* * * * *